United States Patent
Akiyama et al.

(10) Patent No.: US 8,384,902 B2
(45) Date of Patent: Feb. 26, 2013

(54) OPTICAL GAS-ANALYSIS SYSTEM AND A GAS FLOW CELL

(75) Inventors: Osamu Akiyama, Kyoto (JP); Tsuyoshi Moriya, Tokyo (JP); Jun Yamawaku, Nirasaki (JP)

(73) Assignees: Shimadzu Corporation, Kyoto (JP); Tokyo Electron Limited, Tokyo (JP)

( * ) Notice: Subject to any disclaimer, the term of this patent is extended or adjusted under 35 U.S.C. 154(b) by 422 days.

(21) Appl. No.: 12/724,034

(22) Filed: Mar. 15, 2010

(65) Prior Publication Data

US 2010/0238446 A1 Sep. 23, 2010

(30) Foreign Application Priority Data

Mar. 17, 2009 (JP) ................................ 2009-064920

(51) Int. Cl.
*G01N 21/00* (2006.01)
(52) U.S. Cl. ...................................................... 356/437
(58) Field of Classification Search .................... 356/437
See application file for complete search history.

(56) References Cited

U.S. PATENT DOCUMENTS

| | | | | |
|---|---|---|---|---|
| 5,867,329 A * | 2/1999 | Justus et al. | .................. | 359/861 |
| 5,929,981 A * | 7/1999 | Keilbach | .......................... | 356/73 |
| 6,937,324 B2 * | 8/2005 | Kameoka | ......................... | 356/73 |
| 2003/0184733 A1 * | 10/2003 | Kameoka | ......................... | 356/73 |

FOREIGN PATENT DOCUMENTS

| | | |
|---|---|---|
| JP | 2006-058009 A | 3/2006 |
| JP | 2009047612 A  * | 3/2009 |

* cited by examiner

*Primary Examiner* — Roy M Punnoose
(74) *Attorney, Agent, or Firm* — Sughrue Mion, PLLC

(57) ABSTRACT

A gas flow cell for an optical gas-analysis system, including a cylindrical cell body; and a single sample-gas introduction port configured to introduce sample-gas. The single sample-gas introduction port is provided at a location at a substantial center of the cell body with respect to a long axis direction of the cell body, and the single sample-gas introduction port is aligned along a direction orthogonal to the long axis direction so that the cylindrical cell body and the single sample-gas introduction port together form a shape of a character T.

20 Claims, 11 Drawing Sheets

OPTICAL GAS-ANALYSIS SYSTEM AND A GAS FLOW CELL

CROSS REFERENCE TO RELATED APPLICATIONS AND INCORPORATION BY REFERENCE

This application claims benefit of priority under 35 USC 119 based on Japanese Patent Application No. P2009-064920 filed on Mar. 17, 2009, the entire contents of which are incorporated by reference herein.

BACKGROUND OF THE INVENTION

1. Field of the Invention

The present invention pertains to an optical gas-analysis system, and more particularly relates to an optical gas-analysis system suitable for an in-line analysis system of a process chamber that uses a gas in a semiconductor manufacturing equipment and the like, and a gas flow cell used in the optical gas-analysis system.

2. Description of the Related Art

In an earlier multiple-reflection cell of Herriot type, as illustrated in FIGS. 11 and 12, opposite two mirrors of first cell mirror 41 and second cell mirror 42 are placed in a cell body 53, and light enters between two of the first cell mirror 41 and second cell mirror 42 through a hole bored in the first cell mirror 41, and the light is multiple-reflected between two of the first cell mirror 41 and second cell mirror 42, and the multiple-reflected light is extracted from the hole bored in the first cell mirror 41. In a gas flow cell 1x illustrated in FIG. 11, in order to smoothly exchange sample-gases, a sample-gas introduction port 18 and a sample-gas exhaust port 19 prepared for sample-gases are arranged in a diagonal direction as recited in JP 2006-58009A. In a configuration of another gas flow cell 1y illustrated in FIG. 12, in which the sample-gas introduction port 18 and the sample-gas exhaust port 19 prepared for sample-gases are arranged on the same side of the cell body 53, the sample-gas introduction port 18 and the sample-gas exhaust port 19 are respectively arranged at portions close to both ends of the cell body 53.

As illustrated in FIGS. 11 and 12, when the sample-gas introduction port 18 and the sample-gas exhaust port 19 prepared for sample-gases are allocated in the diagonal-direction topology or the portions close to both the ends of the cell, and when particles (particulate matters) exist in the sample-gas, as in a semiconductor manufacturing process, a branched tube for the sample-gas introduction port 18 or a branched tube for the sample-gas exhaust port 19 and the first cell mirror 41 and the second cell mirror 42 are closely located. Thus, the particles are easily deposited on surfaces of the first cell mirror 41 and the second cell mirror 42. When the particles are deposited on the surfaces of the first cell mirror 41 and the second cell mirror 42, ascribable to the effect of the multiple-reflection of light, the effective reflection-capabilities of the first cell mirror 41 and the second cell mirror 42 are reduced, and the sensibilities are dropped.

Although the Herriot multiple-reflection cell is represented in FIGS. 11 and 12, another gas-analysis system of absorption-spectrophotometry, such as a gas-analysis system of White multiple-reflection absorption-spectrophotometry and the like, have also similar problems. Furthermore, in optical gas-analysis systems of emission-spectrometry, fluorescent-photometry and the like, other than absorption-spectrophotometry, in general, as in the case of gas analysis of semiconductor manufacturing process, when particles (particulate matters) exist in sample-gas, there is a problem that the particles are apt to be deposited on the surface of a mirror, an optical window or the like, which is disposed at a position close to the branched tube of an inlet or the branched tube of an outlet.

In particular, in the multiple-reflection gas-analysis system, such as the gas-analysis system of the multiple-reflection absorption-spectrophotometry and the like, the effective reflection-capability of the mirror is decreased, as represented by the power of the number of the reflections of light. Thus, because decrease of the effective reflection-capability of the mirror results in a great drop in the sensibility of the gas-analysis system, even a slight particle deposition on the mirror causes the output light quantity from the cell to be decreased to approximately zero.

In view of the above-mentioned problems, an object of the present invention is to provide an optical gas-analysis system and a gas flow cell to be used in the optical gas-analysis system, in which surfaces of mirrors located at both ends of the gas flow cell, an optical window of the gas flow cell, or the like, are prohibited from being contaminated by particles generated in the inside of a process chamber to be examined, from which sample-gas is introduced, so that the sensibility of the optical gas-analysis system is not dropped, and as a result, an accurate gas analysis with high sensibility of the sample-gas in the inside of the process chamber can be achieved and continued, by establishing an accurate in-line monitoring of the sample-gas.

SUMMARY OF THE INVENTION

A first aspect of the present invention is a gas flow cell for an optical gas-analysis system, including a cylindrical cell body; and a single sample-gas introduction port configured to introduce sample-gas. The single sample-gas introduction port is provided at a location at a substantial center of the cell body with respect to a long axis direction of the cell body, and the single sample-gas introduction port is aligned along a direction orthogonal to the long axis direction so that the cylindrical cell body and the single sample-gas introduction port together form a shape of a character T.

A second aspect of the present invention is a gas flow cell for an optical gas-analysis system including a cylindrical cell body; a sample-gas introduction port configured to introduce sample-gas and a sample-gas exhaust port configured to exhaust the sample-gas, the sample-gas introduction port and the sample-gas exhaust port provided respectively at locations at a substantial center of the cell body with respect to a long axis direction of the cell body, and each of the sample-gas introduction port and the sample-gas exhaust port is aligned along the direction orthogonal to the long axis direction so that the cylindrical cell body, the sample-gas introduction port, and the sample-gas exhaust port together form a cross-shaped configuration; first and second flanges disposed at both ends of cell body, respectively; a first cell mirror provided to a surface of the first flange; and a second cell mirror provided to a surface of the second flange so that a mirror surface of the second cell mirror faces to a mirror surface of the first cell mirror, defining an inter-mirror distance between the first and second mirrors.

A third aspect of the present invention is an optical gas-analysis system, including a cylindrical cell body; a single sample-gas introduction port configured to introduce sample-gas, the single sample-gas introduction port provided at a location at a substantial center of the cell body with respect to a long axis direction of the cell body, and the single sample-gas introduction port being aligned along a direction orthogonal to the long axis direction so that the cylindrical cell body and the single sample-gas introduction port together form a shape of a character T; and a photo-electric conversion chamber configured to convert optical information from the gas flow cell into electric signals.

A fourth aspect of the present invention is an optical gas-analysis system, including a cylindrical cell body; a sample-gas introduction port configured to introduce sample-gas and a sample-gas exhaust port configured to exhaust the sample-gas, the sample-gas introduction port and the sample-gas exhaust port provided respectively at locations at a substantial center of the cell body with respect to a long axis direction of the cell body, and each of the sample-gas introduction port and the sample-gas exhaust port being aligned along the direction orthogonal to the long axis direction so that the cylindrical cell body, the sample-gas introduction port, and the sample-gas exhaust port together form a cross-shaped configuration; first and second flanges disposed at both ends of cell body, respectively; a first cell mirror provided to a surface of the first flange; a second cell mirror provided to a surface of the second flange so that a mirror surface of the second cell mirror faces to a mirror surface of the first cell mirror, defining an inter-mirror distance between the first and second mirrors; and a photo-electric conversion chamber configured to convert optical information from the gas flow cell into electric signals.

BRIEF DESCRIPTION OF THE DRAWINGS

Various embodiments of the present invention will be described with reference to the accompanying drawings. It is to be noted that the same or similar reference numerals are applied to the same or similar parts and elements throughout the drawings, and the description of the same or similar parts and elements will be omitted or simplified. Generally and as it is common in the representation of optical system, it will be appreciated that the various drawings are not drawn to scale from one figure to another nor inside a given figure, and in particular that the layer thicknesses of the constituent member are arbitrarily drawn for facilitating the reading of the drawings.

DETAILED DESCRIPTION OF THE INVENTION

First and second embodiments of the present invention will be described below with reference to the drawings. In the following description, specific details are set forth, such as specific materials, processes and equipment in order to provide a thorough understanding of the present invention. It will be apparent, however, to one skilled in the art that the present invention may be practiced without these specific details. In other instances, well-known manufacturing materials, processes and equipment are not set forth in detail in order not to unnecessarily obscure the present invention. Preposition of "on" is defined with respect to a subject plane, regardless of the orientation in which the subject plane is actually held.

First Embodiment

Figure 1:
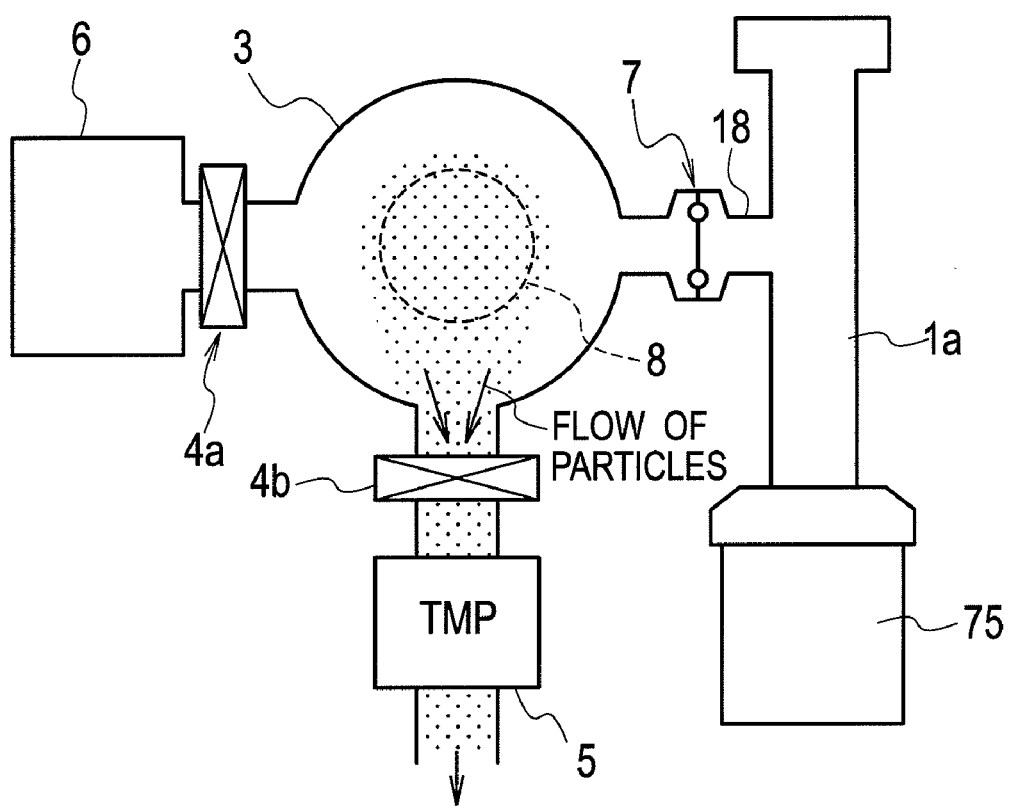
FIG. 1 is a schematic view describing an outline of a structure of an in-line analysis system that uses an optical gas-analysis system pertaining to a first embodiment of the present invention.

As illustrated in FIG. 1, an optical gas-analysis system (1a, 75) pertaining to a first embodiment of the present invention is directed to an gas-analysis system of absorption-spectrophotometry, which encompasses a gas flow cell 1a implemented by a T-shaped configuration (hereinafter, referred to as "T-shaped gas flow cell 1a") and a light source chamber (a photo-electric conversion chamber) 75 attached to the T-shaped gas flow cell 1a, configured to convert optical information sent from the T-shaped gas flow cell 1a into electric signals. To the T-shaped gas flow cell 1a, a single sample-gas introduction port 18, configured to introduce measurement gas or sample-gas to be measured, is assembled so as to implement the T-shaped configuration, The T-shaped gas flow cell 1a is established by Herriot multiple-reflection cell, and the entire configuration of which is established by T-shaped topology, although the detail of the configuration will be described later by using FIG. 3. The sample-gas introduction port 18 of the T-shaped gas flow cell 1a is allocated at an approximate central position, or at a location of a substantial center, along the long axis direction of the T-shaped gas flow cell 1a, such that the sample-gas introduction port 18 is aligned along a direction orthogonal to the long axis direction. Then, through a vacuum coupling 7, a portion (right-side portion in FIG. 1) of the process chamber 3 is directly connected to the end of the sample-gas introduction port 18, which is attached to the T-shaped gas flow cell 1a so as to implement the optical gas-analysis system, and thereby, the in-line analysis system is assembled. In addition, although FIG. 1 exemplifies a vacuum quick-release coupling of an O-ring clamped type as the vacuum coupling 7, the vacuum quick-release coupling may be changed to equivalent various other vacuum fittings, which are known to persons skilled in the art, such as metallic-gasket vacuum joints and the like.

Through a gate valve 4a, another portion (left-side portion in FIG. 1) of the process chamber 3, opposite to the portion of the vacuum coupling 7, is connected to a loading-chamber 6. Furthermore, through a gate valve 4b, a still another portion (bottom-side portion in FIG. 1) of the process chamber 3 orthogonal to the line along the gate valve 4a and the vacuum coupling 7 is further connected to a vacuum pump 5 such as a turbo molecule pump (TMP) or the like. A wafer 8 made of silicon (Si), gallium arsenide (GaAs) and the like is set (loaded) into the loading-chamber 6 when the inside of the loading-chamber 6 is exposed to air. After the wafer 8 is loaded into the loading-chamber 6, the loading-chamber 6 is pre-evacuated by a roughing vacuum pump, although the illustration of the roughing vacuum pump is omitted. When the inner pressure in the loading-chamber 6 reaches to a desired pressure, or to a predetermined pressure, the gate valve 4a is opened, and the wafer 8 is transferred through the gate valve 4a into in the inside of the process chamber 3. The inside of the process chamber 3 can be vacuum-evacuated by the vacuum pump 5 through the gate valve 4b. The pressure in the inside of the process chamber 3 is monitored by a pressure gauge whose illustration is omitted, and a specific gas component, for example, a residual water molecules or the like is monitored by the gas-analysis system of absorption-spectrophotometry (1a, 75). After the inside of the process chamber 3 has been confirmed to be vacuum-evacuated to a predetermined ultimate pressure by the vacuum pump 5, and the specific gas component has been confirmed to reach to the predetermined level or less by the gas-analysis system of absorption-spectrophotometry (1a, 75), reaction-gas is introduced, through a reaction-gas introduction port, into the inside of the process chamber 3, though the illustration of the reaction-gas introduction port is omitted. The inside of the process chamber 3 is vacuum-evacuated to a predetermined processing pressure by the vacuum pump 5. Then, thermal reaction, plasma reaction or photo-excited reaction is used to execute a semiconductor process such as chemical vapor phase deposition (CVD), etching and the like. Then, the gas-analysis system of absorption-spectrophotometry (1a, 75) pertaining to the first embodiment of the present invention directly monitors the gas in the inside of the process chamber 3 through the T-shaped gas flow cell 1a and executes an in-line monitor of reaction in the inside of the process chamber 3, by which the gases employed in a semiconductor manufacturing equipment and the like are monitored.

Figure 2:
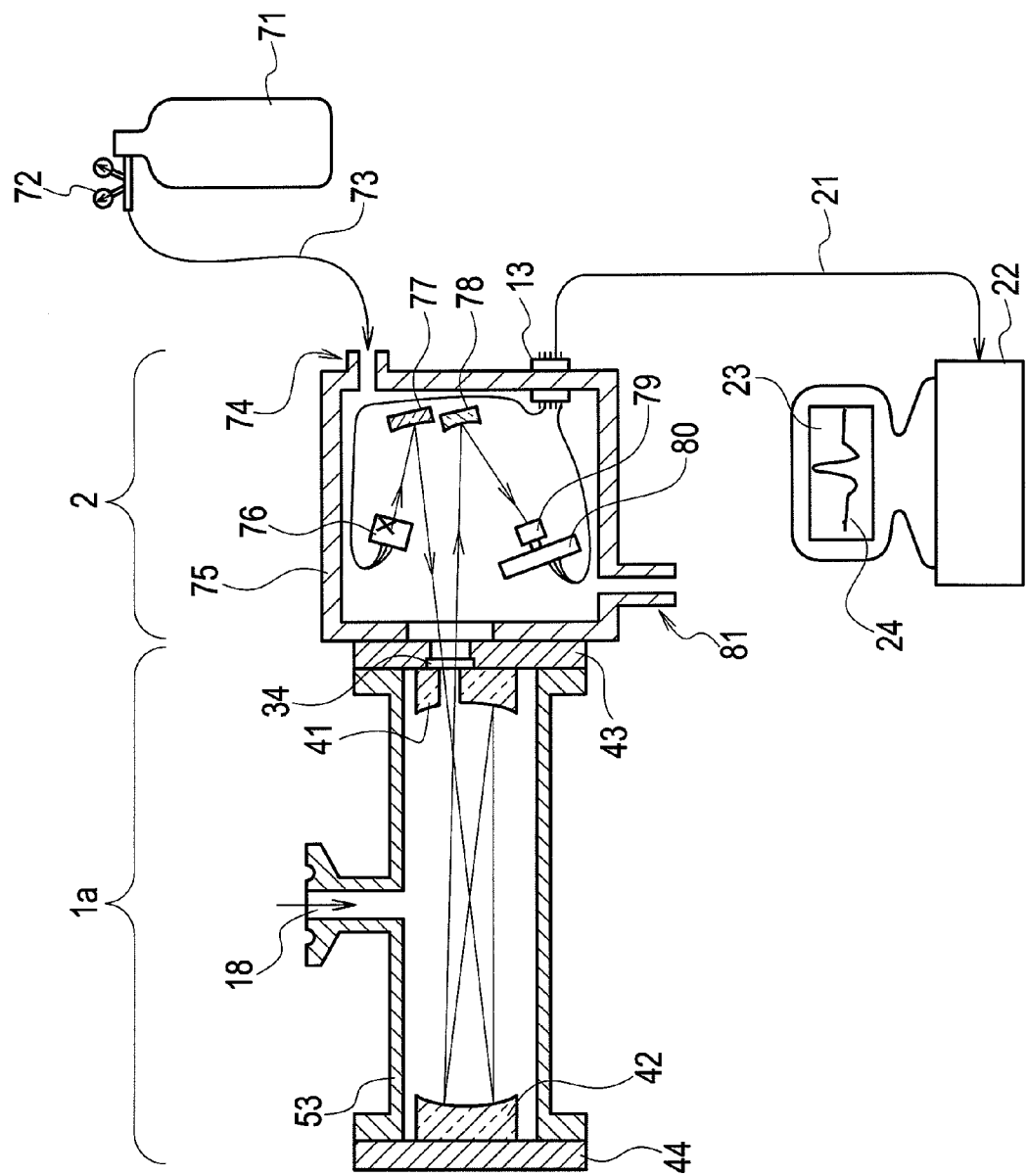
FIG. 2 is a schematic partial sectional view describing an outline of the structure of the optical gas-analysis system pertaining to the first embodiment of the present invention.

As illustrated in FIG. 2, in the inside of the light source chamber (photo-electric conversion chamber) 75, a laser as a light source 76, a light source mirror 77 for reflecting light flux implemented by laser light emitted from the light source 76 so as to introduce the reflected light flux into the T-shaped gas flow cell 1a, a detector mirror 78 for reflecting the light flux returned from the T-shaped gas flow cell 1a, and a light detector 79 for detecting the light flux reflected by the detector mirror 78 and photo-electrically converting optical information detected by the light detector 79 into electric information are installed The reason why the laser is used for the light source 76 is that in a lamp light source such as a halogen lamp or the like, while the lights are multiple-reflected between the first cell mirror 41 and the second cell mirror 42, the dispersion of the light flux becomes great, which disables the sufficient light quantity to be taken out from an output hole.

To the light source chamber (photo-electric conversion chamber) 75, a purge gas introduction port 74 and a purge gas exhaust port 81 are provided. Pressure of nitrogen gas ($N_2$) from a nitrogen gas cylinder 71 is reduced to a predetermined pressure by a pressure-reducing valve 72 and nitrogen gas is supplied through a purge gas supply line 73 to the purge gas introduction port 74. In FIG. 2, the scheme for the nitrogen gas purge in the inside of the light source chamber 75 is represented by a simple gas-flow configuration. In short, although a pressure-maneuvering valve for increasing, adjusting or holding the inner pressure of the light source chamber 75 is not illustrated on the side of the purge gas exhaust port 81, the pressure-maneuvering valve may be provided to the side of the purge gas exhaust port 81.

The light flux emitted from the light source 76 passes through a light transmission hole cut in a first flange 43 and a light transmission window 34 embedded at the rear of the first cell mirror 41 and enters through a light transmission hole bored in the first cell mirror 41 to a cell body 53. After the light flux is multiple-reflected between the first cell mirror 41 and the second cell mirror 42 that implement reflection surfaces of the cell body 53, the light flux is again extracted from the light transmission hole, the light transmission window 34 and the light transmission hole. After that, the light flux is photo-electrically converted into an electric signal by the light detector 79. After the electric signals are amplified by a pre-amplifier 80 connected to the light detector 79, the electric signals are taken out to the outside of the light source chamber 75 through a hermetically sealed connector 13, and, through a signal cable 21, are fed into a controller 22. Inside the controller 22, the electric signals are amplified and processed by a known signal processing circuit and become signals representing component concentration of the sample-gas (hereinafter called as "concentration signals"), and a spectral 24 indicating the concentration signals is displayed on a CRT 23.

Figure 3:
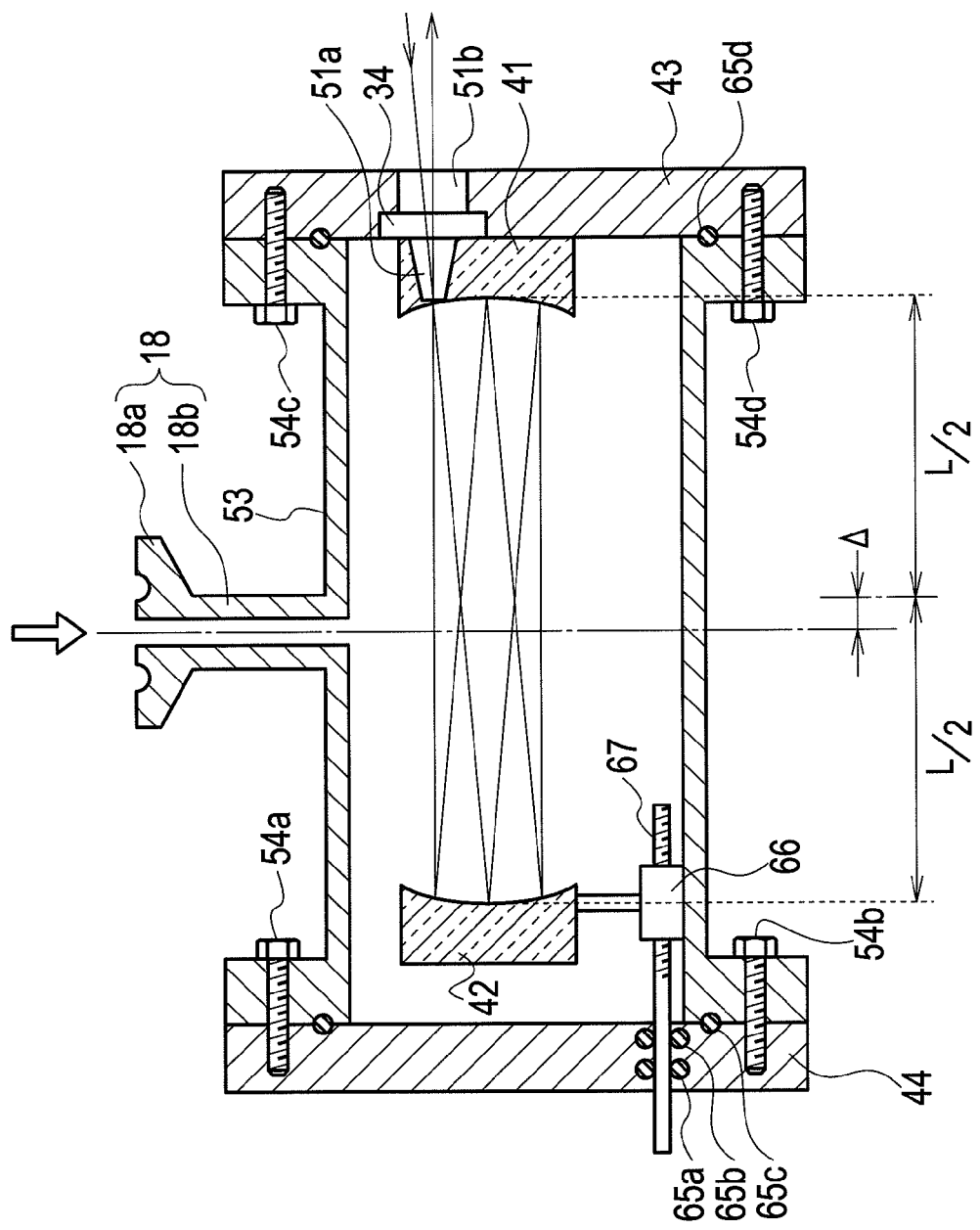
FIG. 3 is a schematic sectional view describing an outline of a structure of a T-shaped gas flow cell that is used in the optical gas-analysis system pertaining to the first embodiment of the present invention.

As illustrated in FIG. 3, the T-shaped gas flow cell 1a pertaining to the first embodiment includes a cylindrical cell body 53, a first flange 43, a second flange 44, a first cell mirror 41 fixed to or formed into a single unit with the first flange 43, and a second cell mirror 42 integrated with but movable against the second flange 44. The first flange 43 and second flange 44 encapsulate a couple of ends of the cell body 53. The first flange 43 is fixed, through an O-ring 65d, to the cell body 53 with fixing screws 54c, 54d. And the second flange 44 is fixed, through an O-ring 65c, to the cell body 53 with fixing screws 54a, 54b. The first cell mirror 41 and the second cell mirror 42 are oppositely arranged such that the concave mirror surfaces of the first cell mirror 41 and the second cell mirror 42 face each other in the inside of the cell body 53.

The gas flow cell 1a illustrated in FIG. 3 is designed such that the whole of the second cell mirror 42 is mounted on a support base 66, which is driven by a liner driver along the long axis direction of the cell body 53. A guide screw 67 may implement the liner driver. That is, the guide screw 67 rotates so that the second cell mirror 42 can travel by sliding, facilitating the adjustment of the distance between the first cell mirror 41 and the second cell mirror 42. The guide screw 67 is formed partially at a part of a length of a cylindrical shaft, and the cylindrical shaft rotates around an axis along a vertical direction to the surface of the second flange 44, supported by a penetrating cylinder bored in the second flange 44, while keeping the vacuum sealing between the cylindrical shaft and the second flange 44 through O-rings 65a, 65b.

A first light-transmission hole 51a is bored in the first cell mirror 41, and a second light-transmission hole 51b is bored in the first flange 43. Furthermore, a light transmission window 34 made of quartz glass is embedded in a recess cut at rear side of the first cell mirror 41, so that the light transmission window 34 can hermetically contact to the first cell mirror 41. The light passes through the second light-transmission hole 51b and the light transmission window 34, which are provided in the first flange 43, and enters from the first light-transmission hole 51a bored in the first cell mirror 41 to the inside of the cell body 53. After the light is multiple-reflected by the concave mirror surfaces of the first cell mirror 41 and the second cell mirror 42, the multiple-reflected light is again extracted through the first light-transmission hole 51a, the light transmission window 34 and the second light-transmission hole 51b to the outside. The first light-transmission hole 51a and the second light-transmission hole 51b serve not only as the entrance holes of the light but also as the exit holes.

In the cell body 53, the sample-gas introduction port 18 configured to introduce the sample-gas to be measured is arranged at a location of the substantial center of the cylindrical cell body 53. With respect to the longitudinal direction of the cell body 53, the sample-gas introduction port 18 is vertically branched so as to implement the shape of a character T. "Substantial center" implies that, when an inter-mirror distance between the first cell mirror 41 and the second cell mirror 42 is assumed to be L, an allowable distance $\Delta$:

$$\Delta = \pm 0.2L$$

from the absolute center between the first cell mirror 41 and the second cell mirror 42 can be allowed as the maximum displacement. In the in-line analysis system pertaining to the first embodiment, when the sample-gas to be measured is introduced from the sample-gas introduction port 18, the probability of particle introduction into the T-shaped gas flow cell 1a is small, the particles are generated in the inside of the process chamber 3, as compared with an in-line analysis system according to a second embodiment, which will be described later. However, even in the in-line analysis system pertaining to the first embodiment, there is a fear that the more minute particles may be diffused at length near to the allowable distance $\Delta$ from the sample-gas introduction port 18 toward both ends in the inside of the gas flow cell 1a. The diffusion length at which the particles are diffused from the sample-gas introduction port 18 toward both the ends, in the inside of the gas flow cell 1a, have a relationship with the inter-mirror distance L between the first cell mirror 41 and the second cell mirror 42, and the diffusion length is about 20% of the inter-mirror distance L, according to the experiment of the inventors of the present invention.

The sample-gas introduction port 18 encompasses a sample-gas introduction flange 18a and a sample-gas introduction branched tube 18b. As for the sample-gas introduction port 18, FIG. 1 exemplifies the case that the sample-gas introduction port 18 is connected through the vacuum coupling 7 to the process chamber 3. Thus, an O-ring groove is cut in the sample-gas introduction flange 18a. However, when other vacuum sealing materials can be used such as metallic gaskets and the like, the shape of the sample-gas introduction flange 18a naturally changes corresponding to the kind of vacuum sealing materials.

Because the T-shaped gas flow cell 1a pertaining to the first embodiment illustrated in FIG. 3 treats the various sample-gases as target gases to be measured, such as gases used in ranges between atmospheric pressure to vacuum pressure, the cell body 53 of the optical gas-analysis system (1a, 75) has a hermetically sealed structure. Stainless steel (SUS) is used for the materials of the cell body 53, the first cell mirror 41 and the second cell mirror 42, by considering corrosion resistance against active gases.

In the in-line analysis system of the process chamber 3, which analyze the gases employed in the semiconductor manufacturing equipment as illustrated in FIG. 1 and the like, the particles are mainly generated in the inside of the process chamber 3, as the result of the reaction between the reaction-gas and the wafer 8 near the surface of the wafer 8, or the reaction between the reaction-gas and the water molecules adsorbed on the surface of the wafer 8 and the like. Most of the generated particles are quickly sucked and evacuated from the inside of the process chamber 3 by the vacuum pump 5 and sent to the exhaust line side. Thus, the generated particles are hardly sent into the gas flow cell 1a attached through the vacuum coupling 7 to the chamber wall of the process chamber 3. Hence, the influence of the particles on the gas flow cell 1a is little.

However, the gases just on the wafer 8 and just near the wafer 8 are not directly measured by the T-shaped gas flow cell 1a. There remains a problem as to whether or not the gas in the inside of the process chamber 3 is correctly sampled by the T-shaped gas flow cell 1a. However, a region of vacuum level, from which the process is actually started, spans form a high vacuum region to a middle vacuum or more. Then, at the vacuum level of the middle vacuum or more, because the mean free path $\lambda$ of the process gas at a processing pressure P becomes large, and therefore, the gas in the center of the process chamber 3 and the gas inside the T-shaped gas flow cell 1a can become substantially equal in component, there is no problem of erroneously sampling gas in the inside of the process chamber 3 by the T-shaped gas flow cell 1a.

For example, in a case of nitrogen gas or air (the same level from the viewpoint of an order even in the case of the process gas for a semiconductor manufacturing equipment), with a processing pressure P [Pa], a mean free path $\lambda$ [cm] indicating an average traveling distance between successive collisions for a gas molecule is approximately represented by:

$$\lambda = 6.7 \times 10^{-1}/P \qquad (1).$$

For example, in a case of a processing pressure P=0.13 Pa (=1 mTorr), mean free path $\lambda \approx 5$ cm, and in a case of a processing pressure P=0.013 Pa (=0.1 mTorr), mean free path $\lambda \approx 50$ cm.

Thus, when a cell length of the T-shaped gas flow cell 1a is about 30 cm and the sample-gas introduction port 18 is located at the cell center, a distance between the sample-gas introduction port 18 in the gas flow cell 1a and the first cell mirror 41 or between the sample-gas introduction port 18 and the second cell mirror 42 is 15 cm, which indicates the substantially same level as the mean free path $\lambda$. Hence, the components of process gas at a processing pressure P are instantaneously uniformed, after the action of collision and replacement of gas molecules in the inside of the gas flow cell 1a.

As a result, the T-shaped gas flow cell 1a enables the correct light absorption analysis of the process gas to be processed in the inside of the process chamber 3. That is, according to the in-line analysis system pertaining to the first embodiment of the present invention, the surfaces of the first cell mirror 41 and the second cell mirror 42 that are located at both ends of the T-shaped gas flow cell 1a are not contaminated by the particles generated in the inside of the process chamber 3, and the sensibility of the gas-analysis system of absorption-spectrophotometry (1a, 75) is not dropped. Also, the gas analysis substantially equal to the inside of the process chamber 3 can be achieved in the gas-analysis system of absorption-spectrophotometry (1a, 75). Thus, the gas-analysis system of absorption-spectrophotometry (1a, 75) can continue accurate measurements with high sensibility.

Second Embodiment

Figure 4:
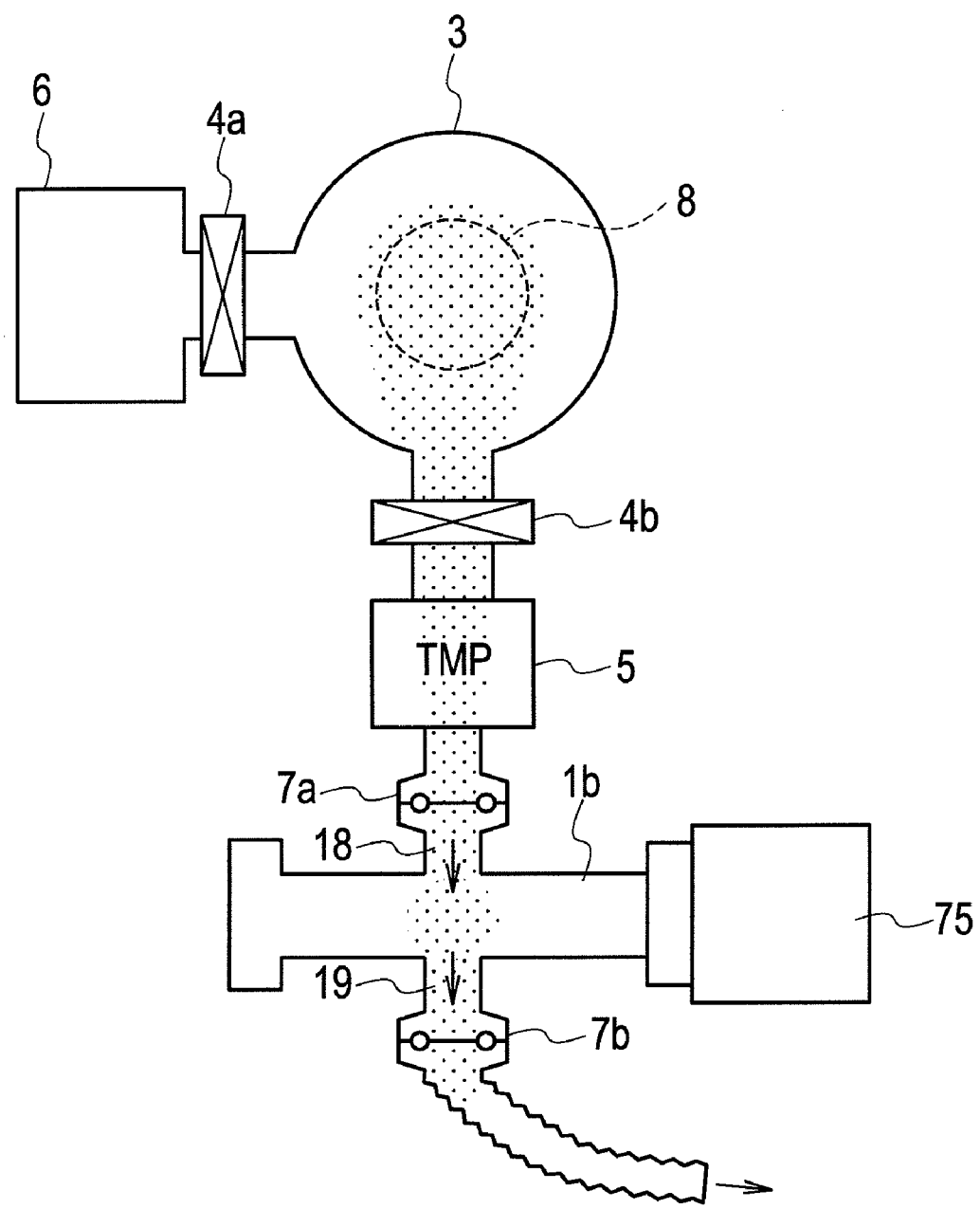
FIG. 4 is a schematic view describing an outline of a structure of an in-line analysis system that uses an optical gas-analysis system pertaining to a second embodiment of the present invention.

As illustrated in FIG. 4, an optical gas-analysis system (1b, 75) pertaining to a second embodiment of the present invention encompasses a gas flow cell having a cross configuration or a cruciform topology (hereinafter, referred to as "cross-shaped gas flow cell 1b") and a light source chamber 75 attached to the cross-shaped gas flow cell 1b, configured to convert optical information from the cross-shaped gas flow cell 1b into electric signals. The cross-shaped gas flow cell 1b includes a sample-gas introduction port 18 configured to introduce sample-gas to be measured and a sample-gas exhaust port 19 configured to exhaust the sample-gas.

Although the detail of the cross-shaped gas flow cell 1b will be described later, at a location of the substantial center in the longitudinal direction of the cross-shaped gas flow cell 1b, the sample-gas introduction port 18 and the sample-gas exhaust port 19 are arranged substantially straightly along the direction orthogonal to the longitudinal direction, respectively, and they exhibit the cross topology. Then, the sample-gas introduction port 18 in the cross-shaped gas flow cell 1b establishing the optical gas-analysis system is connected through a vacuum coupling 7a to the exhaust side of the vacuum pump 5 for vacuum-exhausting the inside of the process chamber 3, and the sample-gas exhaust port 19 is connected through a vacuum coupling 7b to a vacuum piping on an exhaust line side, and the in-line analysis system is assembled. In addition, FIG. 4 exemplifies vacuum quick-release couplings of an O-ring clamped type as the vacuum couplings 7a, 7b, the vacuum quick-release couplings may be changed to equivalent various other vacuum fittings, which are known to persons skilled in the art, such as metallic-gasket vacuum joints and the like, similarly to the first embodiment.

The cross-shaped gas flow cell 1b is the Herriot multiple-reflection cell and connected to the light source chamber 75. Then, the cross-shaped gas flow cell 1b and the light source chamber 75 implement the gas-analysis system of absorption-spectrophotometry (1b, 75).

A portion of the process chamber 3 is connected, through the gate valve 4a, to the loading-chamber 6. And another portion of the process chamber 3 is connected, through the gate valve 4b, to the vacuum pump 5 such as the TMP or the like, similarly to the in-line analysis system pertaining to the first embodiment. The wafer 8 made of Si, GaAs and the like is loaded (installed) into the loading-chamber 6, when the inner side of the loading-chamber 6 is exposed to air. After the wafer 8 is loaded into the loading-chamber 6, the loading-chamber 6 is pre-evacuated by the roughing vacuum pump, although the illustration of which is omitted. When inner pressure of the loading-chamber 6 reaches to the predetermined pressure, the gate valve 4a is opened, and the wafer 8 is transferred through the gate valve 4a to the inside of the process chamber 3. The inside of the process chamber 3 can be vacuum-evacuated by the vacuum pump 5 through the gate valve 4b. The pressure of the inside of the process chamber 3 is monitored by the pressure gauge whose illustration is omitted. The specific gas component, for example, the residual water molecules or the like is monitored by the gas-analysis system of absorption-spectrophotometry (1b, 75). The inside of the process chamber 3 is confirmed to be vacuum-evacuated to the predetermined ultimate pressure by the vacuum pump 5, and the specific gas component is confirmed to reach to the predetermined level or less in the gas-analysis system of absorption-spectrophotometry (1b, 75). After that, the reaction-gas is introduced, through the reaction-gas introduction port, into the process chamber 3, although the illustration of the reaction-gas introduction port is omitted. Then, the inside of the process chamber 3 is vacuum-evacuated to the predetermined processing pressure by the vacuum pump 5. Then, the thermal reaction, the plasma reaction or the photo-excited reaction is used to execute the semiconductor process such as CVD, etching and the like. Then, the gas-analysis system of absorption-spectrophotometry (1b, 75) pertaining to the second embodiment of the present invention directly monitors the gas in the inside of the process chamber 3 through the cross-shaped gas flow cell 1b and carries out the in-line monitor of the reaction in the process chamber 3, by which the gases employed in the semiconductor manufacturing equipment and the like are monitored.

Figure 5:
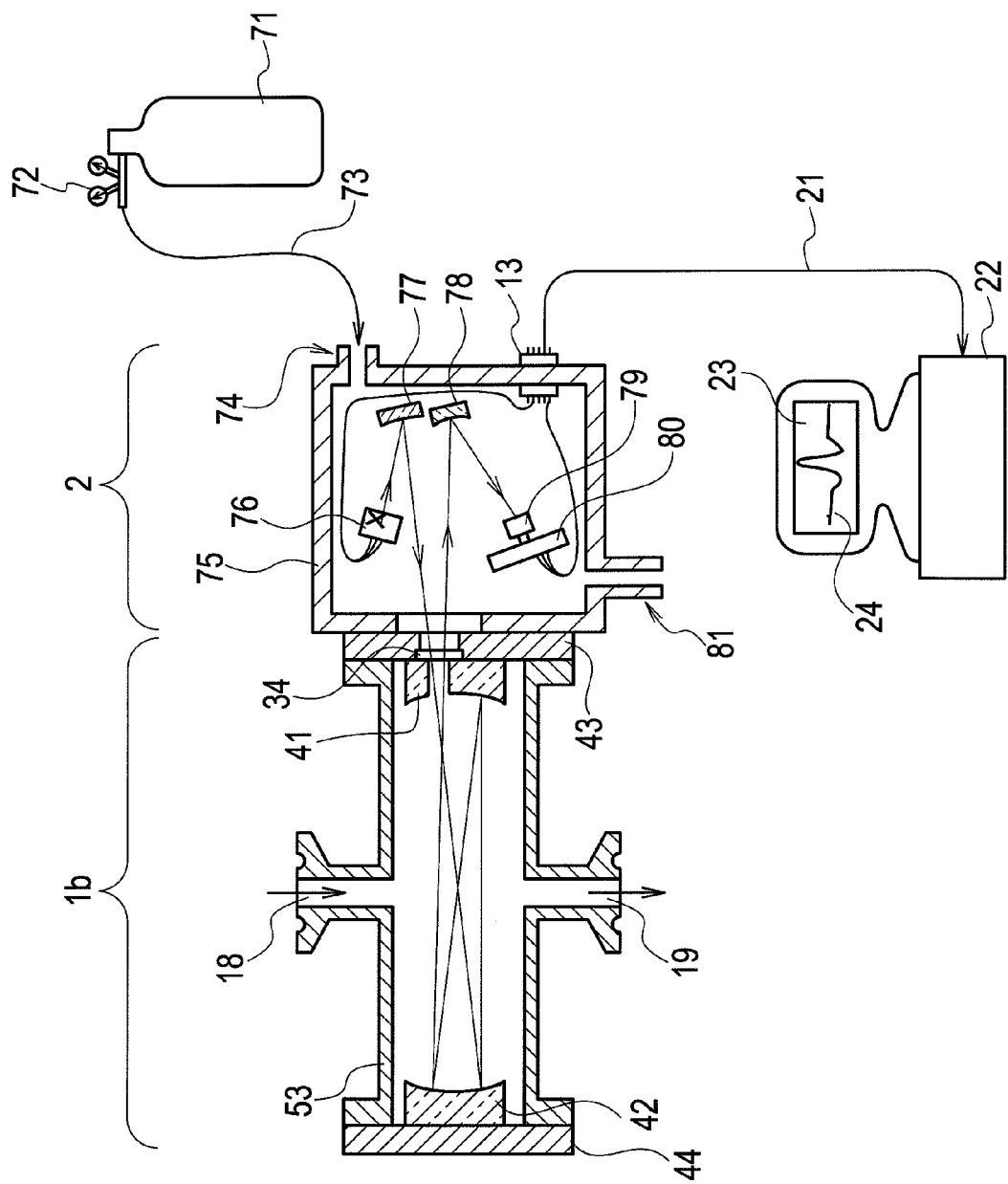
FIG. 5 is a schematic partial sectional view describing an outline of the structure of the optical gas-analysis system pertaining to the second embodiment of the present invention.

In the inside of side the light source chamber 75, a laser as a light source 76, a light source mirror 77 for reflecting light flux implemented by laser light emitted from the light source 76 so as to introduce the light flux into the cross-shaped gas flow cell 1b, a detector mirror 78 for reflecting the light flux returned from the cross-shaped gas flow cell 1b, and a light detector 79 for detecting the light flux reflected by the detector mirror 78 and photo-electrically converting optical information into electric information are installed. A purge gas introduction port 74 and a purge gas exhaust port 81 are provided to the light source chamber 75. Pressure of the nitrogen ($N_2$) gas from a nitrogen gas cylinder 71 is reduced to a predetermined pressure by a pressure-reducing valve 72 and supplied through a purge gas supply line 73 to the purge gas introduction port 74. In FIG. 5, the scheme for the nitrogen gas purge in the inside of the light source chamber 75 is represented by a simple gas-flow configuration. In short, although a pressure-maneuvering valve is not illustrated on the side of the purge gas exhaust port 81, the pressure-maneuvering valve may be attached to the purge gas exhaust port 81.

The light flux emitted from the light source 76 passes through the light transmission hole bored in the first flange 43 and the light transmission window 34 embedded at the rear side of the first cell mirror 41 and enters through the light transmission hole bored in the first cell mirror 41 to the cell body 53. After the light flux is multiple-reflected between the first cell mirror 41 and the second cell mirror 42 that implement the reflection surfaces of the cell body 53, the multiple-reflected light flux is again extracted from the light transmission hole, the light transmission window 34 and the light transmission hole. After that, the multiple-reflected light flux is photo-electrically converted into electrical signals by a light detector 79. After the electric signals are amplified by a pre-amplifier 80 connected to the light detector 79, the electric signals are taken out to the outside of the light source chamber 75 through the hermetically sealed connector 13, and are sent through the signal cable 21 into a controller 22. Inside the controller 22, the electric signals are amplified and processed by the known signal processing circuit and becomes concentration signal, and the spectral 24 indicating the concentration signal is displayed on a CRT 23.

Figure 6:
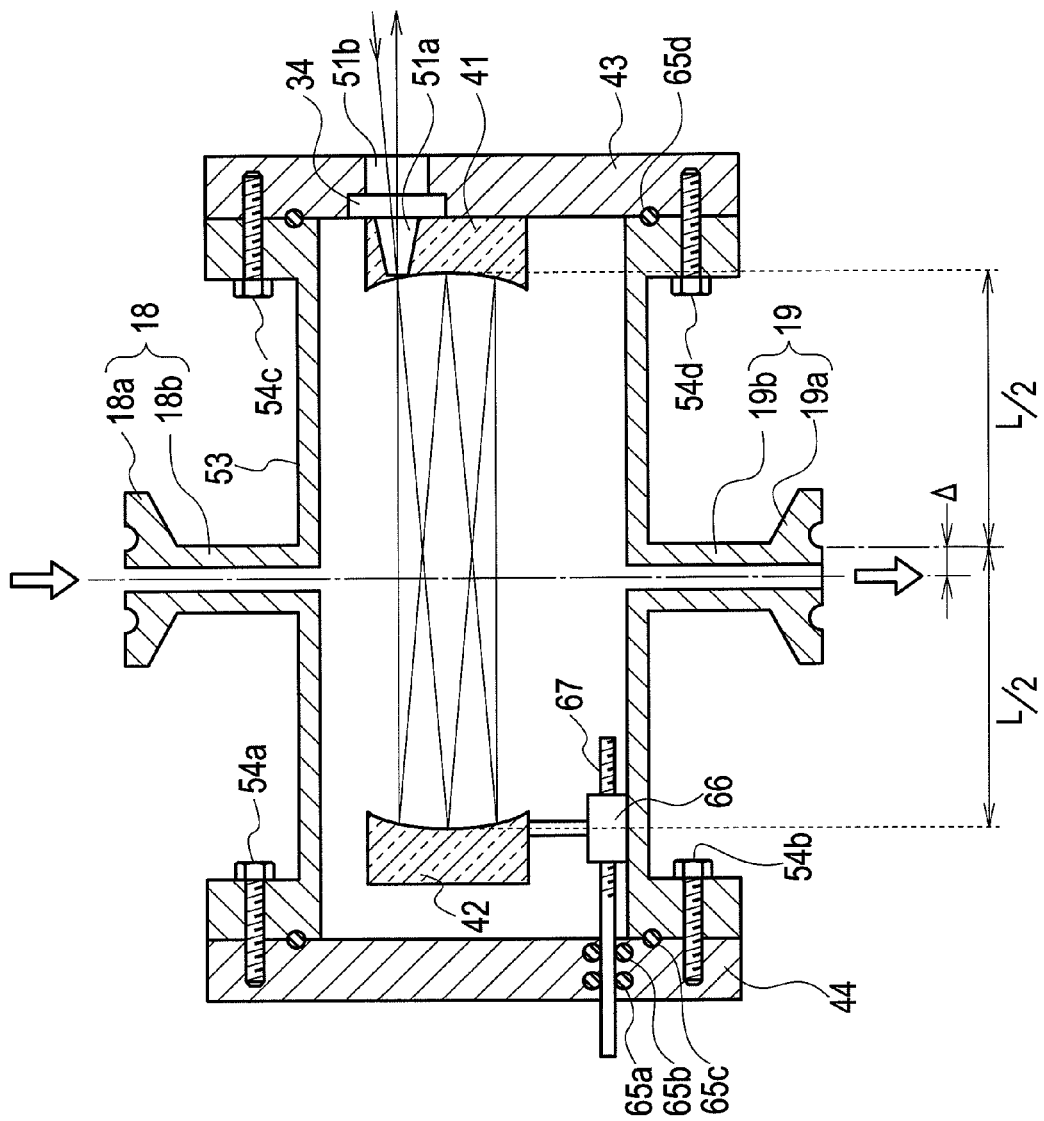
FIG. 6 is a schematic sectional view describing an outline of a structure of a cross-shaped gas flow cell that is used in the optical gas-analysis system pertaining to the second embodiment of the present invention.

As illustrated in FIG. 6, the cross-shaped gas flow cell 1b pertaining to the second embodiment includes the cell body 53, the first flange 43 and the second flange 44 that encapsulate both ends of the cell body 53, the first cell mirror 41 is fastened to or made into a single unit with the first flange 43, and the second cell mirror 42 is provided against the second flange 44. The first cell mirror 41 and the second cell mirror 42 are oppositely arranged such that the concave mirror surfaces of the first cell mirror 41 and the second cell mirror 42 face each other in the inside of the cell body 53.

The gas flow cell 1b illustrated in FIG. 6 is designed such that the whole of the second cell mirror 42 is mounted on a support base 66, which is driven by a guide screw 67. The guide screw 67 rotates so that the second cell mirror 42 can travel by sliding, thereby adjusting the inter-mirror distance L between the first cell mirror 41 and the second cell mirror 42.

A first light-transmission hole 51a is bored in the first cell mirror 41, and a second light-transmission hole 51b is bored in the first flange 43. Furthermore, a light transmission window 34 made of the quartz glass is embedded in a recess cut at the rear side of the first cell mirror 41, so that the light transmission window 34 can hermetically contact to the first cell mirror 41. The light passes through the second light-transmission hole 51b and the light transmission window 34, which are provided in the first flange 43, and enters from the first light-transmission hole 51a bored in the first cell mirror 41 to the inside of the cell body 53. After the light is multiple-reflected on the concave mirror surfaces of the first cell mirror 41 and the second cell mirror 42, the multiple-reflected light is again extracted through the first light-transmission hole 51a, the light transmission window 34 and the second light-transmission hole 51b to the outside of the cross-shaped gas flow cell 1b. The first light-transmission hole 51a and the second light-transmission hole 51b serves not only as the entrance holes of the light but also as the exit holes.

In the cell body 53, the sample-gas introduction port 18 configured to introduce sample-gas to be measured and the sample-gas exhaust port 19 configured to exhaust the sample-gas are arranged substantially straightly at a location of the substantial center of the cylindrical cell body 53. The sample-gas introduction port 18 and the sample-gas exhaust port 19 are arranged such that each of them is cruciformly branched, with respect to the longitudinal direction of the cell body 53. Similarly to the definition in the first embodiment, the "substantial center" implies that a maximum displacement of the location of the sample-gas introduction port 18 and the sample-gas exhaust port 19 within an allowable distance Δ from the absolute center between the first cell mirror 41 and the second cell mirror 42 can be allowed. Where, with the inter-mirror distance L between the first cell mirror 41 and the second cell mirror 42, the allowable distance Δ is defined by:

$$\Delta = \pm 0.2L$$

In the in-line analysis system in the process chamber 3, by which the gases employed in the semiconductor manufacturing equipment and the like are monitored, when the sample-gas to be measured is introduced from the sample-gas introduction port 18 and when the particles generated in the inside of the process chamber 3 are passed through the cross-shaped gas flow cell 1b, the particles are diffused at the diffusion length near to the allowable distance Δ from the sample-gas introduction port 18 toward both the ends of the gas flow cell 1b, in the inside of the gas flow cell 1b.

Figure 7:
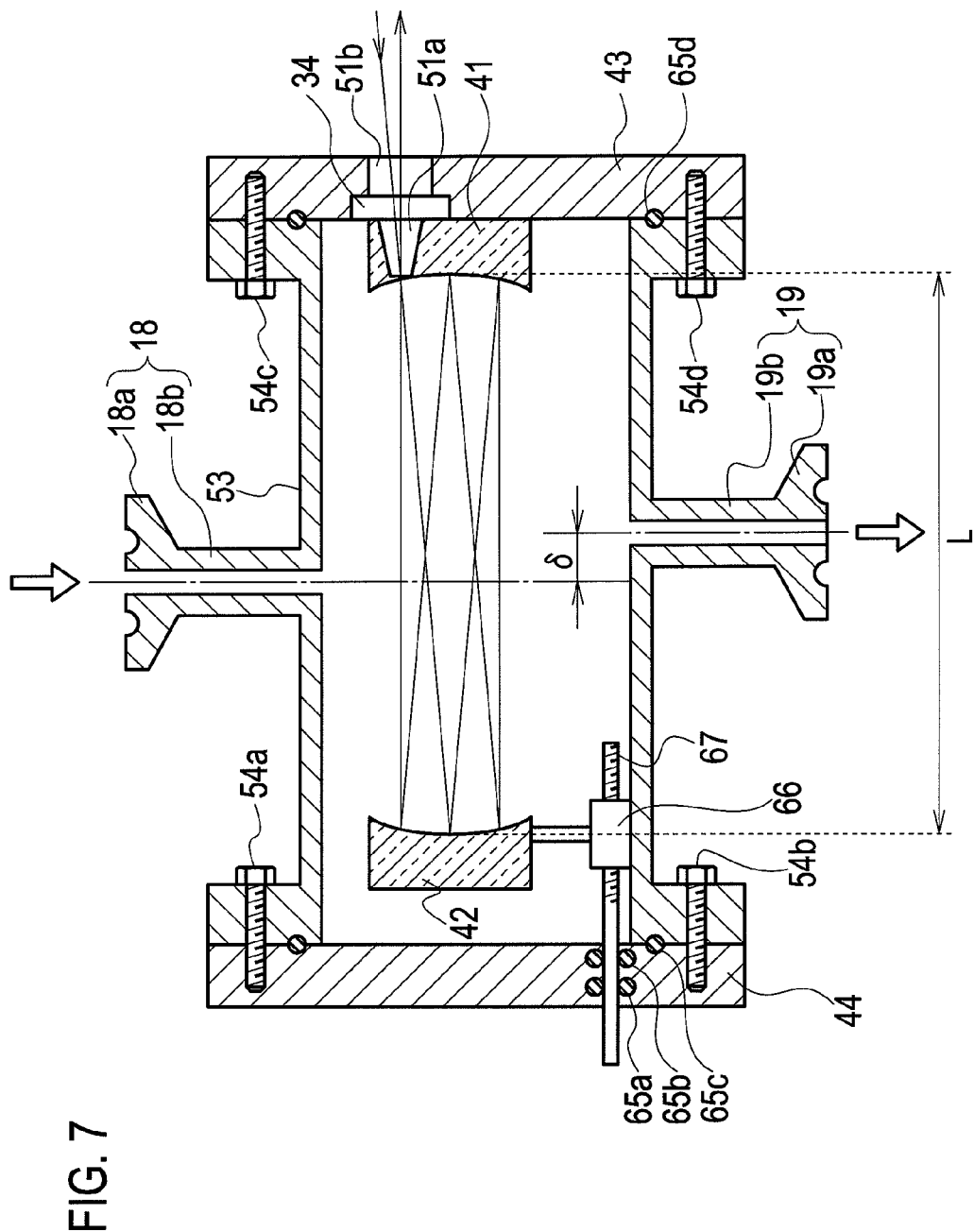
FIG. 7 is a schematic sectional view that describes a displacement length between central lines of a sample-gas introduction port and a sample-gas exhaust port in the cross-shaped gas flow cell which is used in the optical gas-analysis system pertaining to the second embodiment of the present invention.
Figure 8:
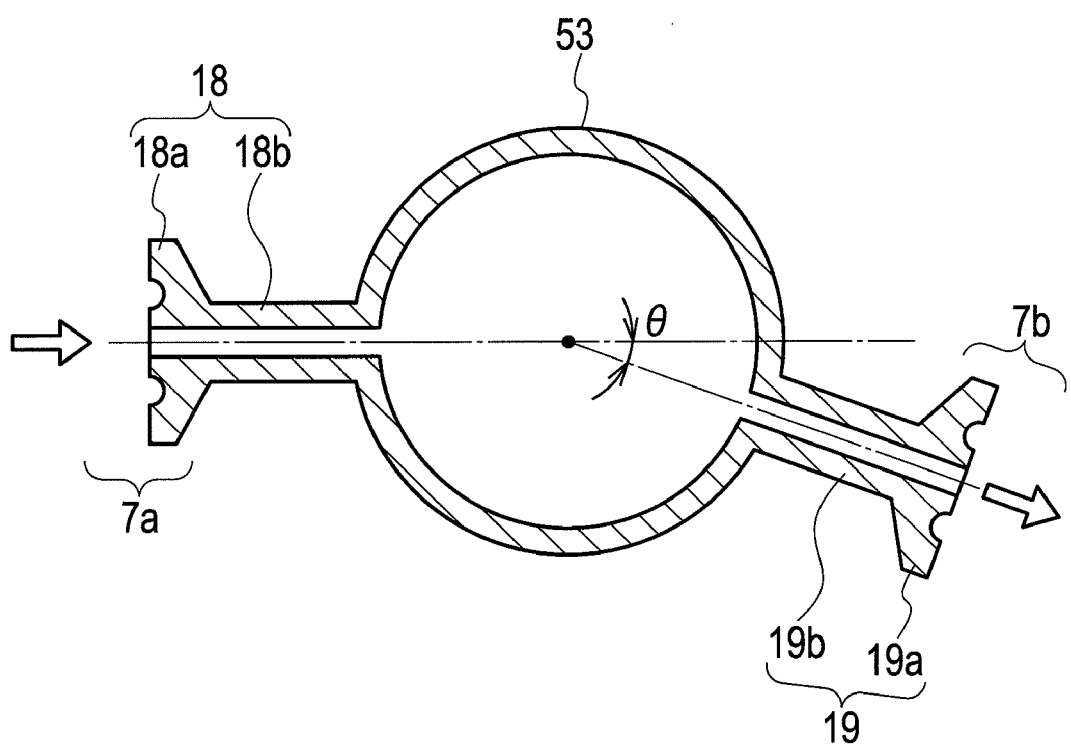
FIG. 8 is a schematic view that describes a displacement angle between the central lines of the sample-gas introduction port and the sample-gas exhaust port in the cross-shaped gas flow cell pertaining to the second embodiment of the present invention, by using a sectional view vertical to a longitudinal direction of the cross-shaped gas flow cell illustrated in FIG. 7.

Also, "substantially straightly" implies, as illustrated in FIG. 7, a displacement length:

$$\delta = \pm 0.2L$$

between the central lines of the sample-gas introduction port 18 and the sample-gas exhaust port 19 is allowed as the maximum displacement. Because, as the displacement length δ between the central lines of the sample-gas introduction port 18 and the sample-gas exhaust port 19 becomes greater than ±0.2 L, the fluid dynamics of the gas flow toward the sample-gas exhaust port 19 from the sample-gas introduction port 18 deviates from laminar-flow regime, the larger displacement length δ is not preferable. However, actually, even when the displacement length δ between the central lines of the sample-gas introduction port 18 and the sample-gas exhaust port 19 is about ±0.2 L, there is a little disturbance from the fluid dynamics of laminar-flow regime in the gas flow toward the sample-gas exhaust port 19 from the sample-gas introduction port 18. Hence, preferably, the displacement length δ between the central lines of the sample-gas introduction port 18 and the sample-gas exhaust port 19 is ±0.1 L or less. Moreover, "substantially straightly" implies that, as illustrated in FIG. 8, a displacement angle θ between the central lines of the sample-gas introduction port 18 and the sample-gas exhaust port 19 is ±10° or less. FIG. 8 is a sectional view vertical to the longitudinal direction of the cross-shaped gas flow cell 1b, namely, a sectional view of the cross-shaped gas flow cell 1b vertical to the direction along the inter-mirror distance L between the first cell mirror 41 and the second cell mirror 42. Because, when the displacement angle θ between the tri central lines of the sample-gas introduction port 18 and the sample-gas exhaust port 19 becomes greater than ±10°, the fluid dynamics of the gas flow toward the sample-gas exhaust port 19 from the sample-gas introduction port 18 deviates from laminar-flow regime, the larger displacement angle θ is not preferable. However, actually, even when the displacement angle θ between the central lines of the sample-gas introduction port 18 and the sample-gas exhaust port 19 is about ±10°, there is a little disturbance from the fluid dynamics of the laminar-flow regime in the gas flow toward the sample-gas exhaust port 19 from the sample-gas introduction port 18. Hence, preferably, the displacement angle θ between the central lines of the sample-gas introduction port 18 and the sample-gas exhaust port 19 is ±5° or less.

Therefore, a topology in which the displacement length δ between the central lines of the sample-gas introduction port 18 and the sample-gas exhaust port 19 is ±0.2 L or less and the displacement angle θ between the central lines of the sample-gas introduction port 18 and the sample-gas exhaust port 19 is ±10° or less is included in the concept of "substantially straightly".

The sample-gas introduction port 18 is implemented by a sample-gas introduction flange 18a and a sample-gas introduction branched tube 18b. The sample-gas exhaust port 19 is implemented by a sample-gas exhaust flange 19a and a sample-gas exhaust branched tube 19b. FIG. 4 exemplifies a case that the sample-gas introduction port 18 in the cross-shaped gas flow cell 1b is connected through the vacuum coupling 7a to the exhaust side of the vacuum pump 5, and the sample-gas exhaust port 19 is connected through the vacuum coupling 7b to the vacuum piping of the exhaust line side. Thus, O-ring grooves are formed in each of the sample-gas introduction flange 18a and the sample-gas exhaust flange 19a, respectively. However, when other vacuum sealing materials can be used such as metallic gaskets and the like, and the shapes of the sample-gas introduction flange 18a and the sample-gas exhaust flange 19a are naturally changed corresponding to the employed kind of vacuum sealing materials.

Even in the in-line analysis system of the process chamber 3, which measurers the gases employed in the semiconductor manufacturing equipment and the like, pertaining to the second embodiment as illustrated in FIG. 4, similarly to the first embodiment, the particles are mainly generated as the result of the reaction between the reaction-gas and the wafer 8 near the surface of the wafer 8, or the reaction between the reaction-gas and the water molecules adsorbed on the surface of the wafer 8 and the like, in the inside of the process chamber 3. The generated particles are sucked and evacuated by the vacuum pump 5. When the exhaust gas including the particles is passed through the vacuum pump 5 and via the cross-shaped gas flow cell 1b, the particles are somewhat diffused toward both ends of the cross-shaped gas flow cell 1b in the inside of the cross-shaped gas flow cell 1b. As mentioned above, the diffusion length at which the particles are diffused from the sample-gas introduction port 18 toward both ends of the cross-shaped gas flow cell 1b, in the inside of the cross-shaped gas flow cell 1b has an relationship with the inter-mirror distance L between the first cell mirror 41 and the second cell mirror 42. In a case of the inter-mirror distance L=about 30 cm, the particles are deposited on a wall surface, at the diffusion length between about 5 and 6 cm from the sample-gas introduction port 18. However, since the first cell mirror 41 and the second cell mirror 42 that are located at both ends of the cross-shaped gas flow cell 1b are sufficiently separated from the sample-gas introduction port 18, there is no deposition on the surfaces of the first cell mirror 41 and the second cell mirror 42. In this way, most of the particles are straightly passed through the portion of the cross-shaped gas flow cell 1b and sent from the sample-gas exhaust port 19 through the vacuum coupling 7b to the exhaust line side. For this reason, the surfaces of the first cell mirror 41 and the second cell mirror 42 that are located at both ends of the cross-shaped gas flow cell 1b are not contaminated, and the sensibility is not dropped.

On the other hand, the exhaust gas components of the process gas are instantaneously evacuated to the outside of the process chamber 3, while repeating the collision and replacement with the residual gas in the inside of the cross-shaped gas flow cell 1b, because the mean free path λ is large, as described above by using the equation (1), in the middle vacuum region at which the process in the process chamber 3 begins. Thus, with the cross-shaped gas flow cell 1b, the light absorption measurement of the gas in the inside of the process chamber 3 can be substantially correctly executed.

As a result, according to the in-line analysis system pertaining to the second embodiment of the present invention, the cross-shaped gas flow cell 1b enables the correct analysis of the light absorption of the process gas in the inside of the process chamber 3. Also, according to the in-line analysis system pertaining to the second embodiment of the present invention, the surfaces of the first cell mirror 41 and the second cell mirror 42 that are located at both ends of the cross-shaped gas flow cell 1b are not contaminated by the particles generated in the inside of the process chamber 3, and the sensibility of the gas-analysis system of absorption-spectrophotometry (1b, 75) is not dropped. Also, the gas analysis substantially equal to the inside of the process chamber 3 can be executed in the gas-analysis system of absorption-spectrophotometry (1b, 75). Thus, the gas-analysis system of absorption-spectrophotometry (1b, 75) can continue accurate measurements with high sensibility.

FIG. 4 exemplifies the case that the absorption-spectrophotometry of the multiple-reflection gas-analysis system that is provided with the cross-shaped gas flow cell 1b is connected through the two couplings 7a, 7b to the exhaust line of the process chamber 3. However, the installed location of the cross-shaped gas flow cell 1b is not limited to the configuration illustrated in FIG. 4.

Figure 9:
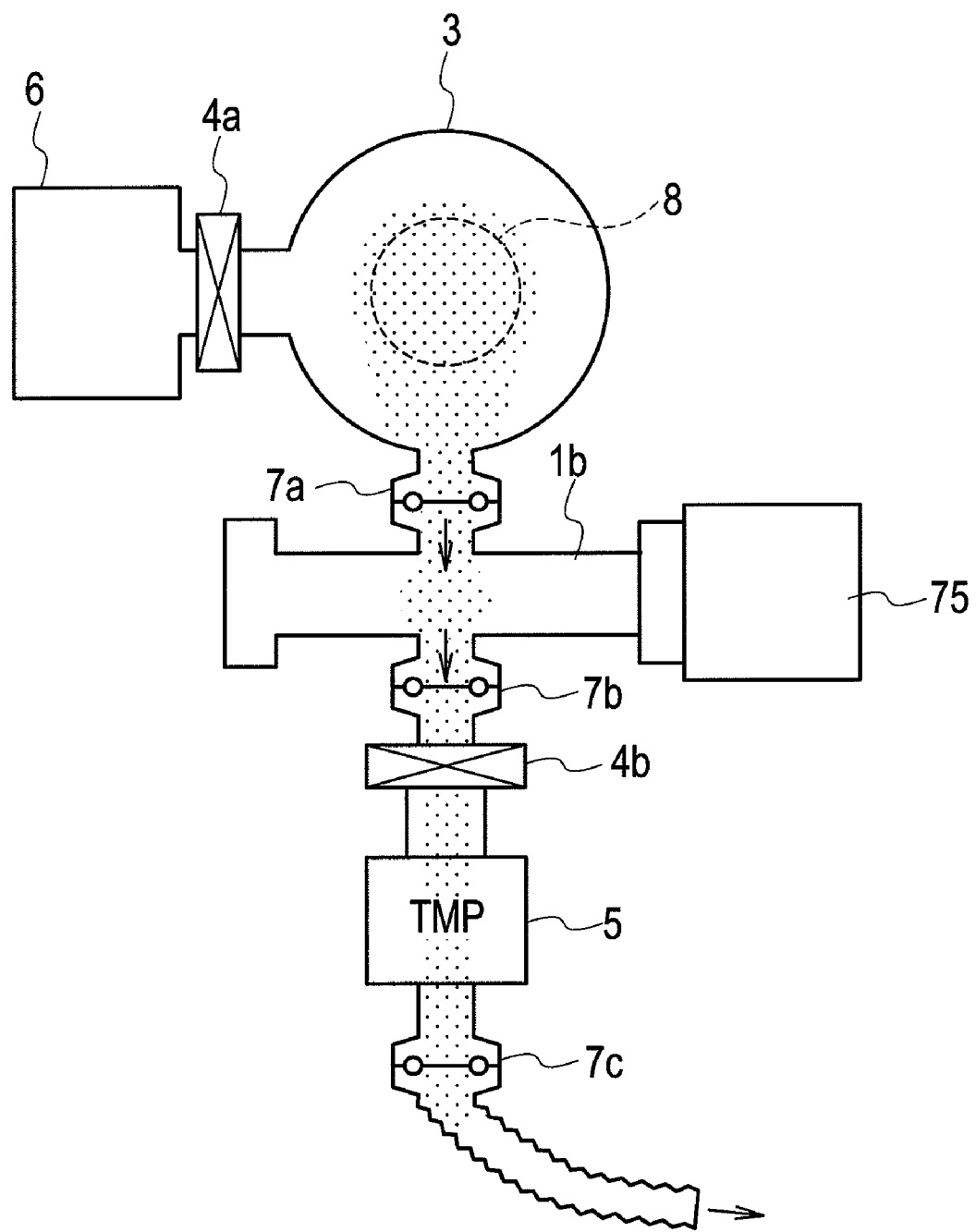
FIG. 9 is a schematic view describing an outline of a structure of an in-line analysis system according to a modification (a first modification) of the second embodiment of the present invention and shows a feature in which the sample-gas introduction port in the cross-shaped gas flow cell is directly connected to an exhaust side of a process chamber and then the sample-gas exhaust port is connected to a sucking side of a gate valve.

For example, as illustrated in FIG. 9, the sample-gas introduction port 18 in the cross-shaped gas flow cell 1b may be directly connected through the vacuum coupling 7a to the exhaust side of the process chamber 3, and the sample-gas exhaust port 19 may be connected through the vacuum coupling 7b to the sucking side of the gate valve 4b.

Figure 10:
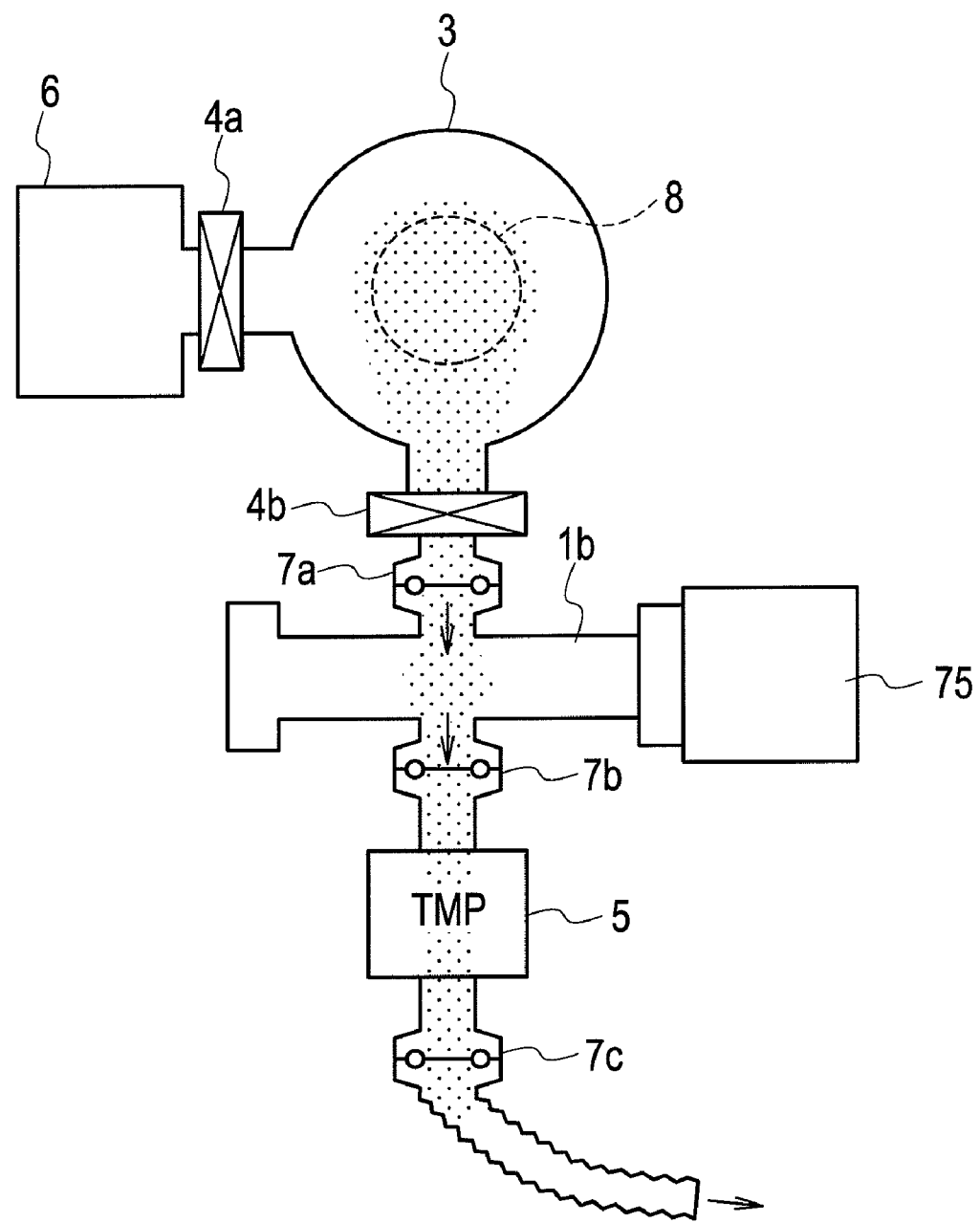
FIG. 10 is a schematic view describing an outline of a structure of an in-line analysis system according to another modification (a second modification) of the second embodiment of the present invention and shows a feature in which the sample-gas introduction port in the cross-shaped gas flow cell is connected to the exhaust side of the gate value and then the sample-gas exhaust port is connected to a sucking side of a vacuum pump.
Figure 11:
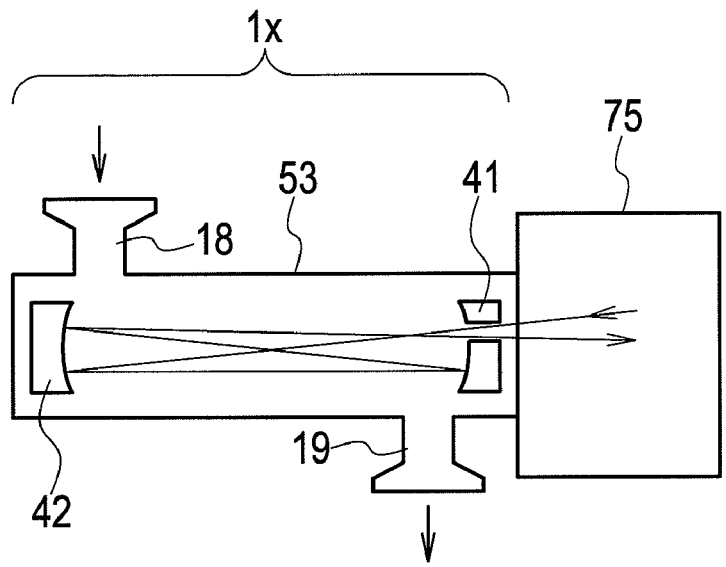
FIG. 11 is a sectional view describing the structure of an earlier multiple-reflection cell of Herriot type.
Figure 12:
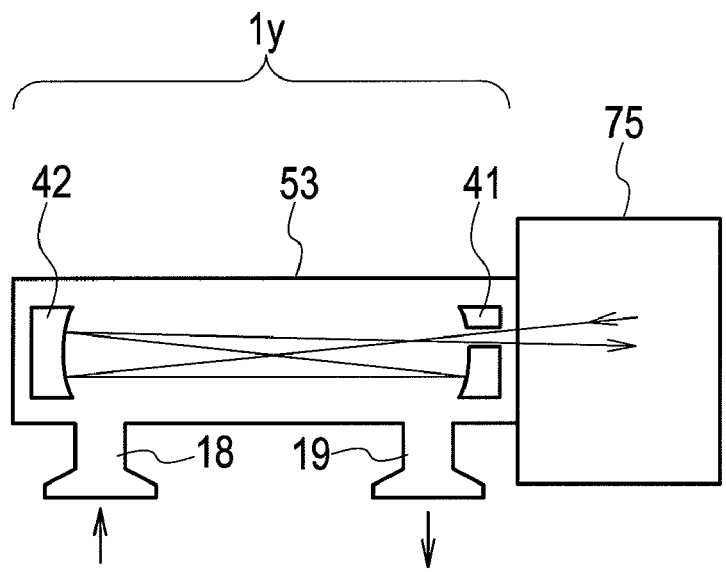
FIG. 12 is a sectional view describing another structure of earlier multiple-reflection cell of the Herriot type.

Alternatively, as illustrated in FIG. 10, the sample-gas introduction port 18 in the cross-shaped gas flow cell 1b may be connected through the vacuum coupling 7a to the exhaust side of the gate valve 4b, and the sample-gas exhaust port 19 may be connected through the vacuum coupling 7b to the sucking side of the vacuum pump 5.

In addition, although FIGS. 9 and 10 exemplify vacuum quick-release couplings of the O-ring clamped type as the vacuum coupling 7a, 7b and 7c, the vacuum quick-release coupling may be changed to equivalent various other vacuum fittings, which are known to persons skilled in the art, such as metallic-gasket vacuum joints and the like, similarly to the cases illustrated in FIGS. 1 and 4.

Other Embodiments

As mentioned above, the present invention has been described on the basis of the first and second embodiments. However, the discussions and drawings serving as a part of the disclosure should not be understood to limit the present invention. Various modifications will become possible for those skilled in the art after receiving the teaching of the present disclosure without departing from the scope thereof.

Although, in the above-mentioned descriptions of the first and second embodiments, Herriot multiple-reflection cells are described, the Herriot multiple-reflection cells are disclosed only as examples. Another gas-analysis system of absorption-spectrophotometry, such as the gas-analysis system of the multiple-reflection absorption-spectrophotometry of White type and the like, is naturally available.

Furthermore, in various optical gas-analysis systems other than the absorption-spectrophotometry, such as gas-analysis systems of emission-spectrometry, fluorescent-photometry and the like, it would be evident from the above-mentioned descriptions that the technical idea of the present invention can be applied to the case having the problem of the in-line monitoring of the sample-gas, in which particles are included, and the particles are apt to be deposited on the surfaces of the mirror, the optical window and the like.

Thus, the present invention of course includes various embodiments and modifications and the like which are not detailed above. Therefore, the scope of the present invention will be defined in the following claims.

What is claimed is:

1. A gas flow cell for an optical gas-analysis system, comprising:
    a cylindrical cell body; and
    a single sample-gas introduction port configured to introduce sample-gas, the single sample-gas introduction port provided at a location at a substantial center of the cell body with respect to a long axis direction of the cell body, and the single sample-gas introduction port being aligned along a direction orthogonal to the long axis direction so that the cylindrical cell body and the single sample-gas introduction port together form a shape of a character T.

2. The gas flow cell of claim 1, further comprising:
first and second flanges disposed at both ends of the cell body, respectively;
a first cell mirror provided to a surface of the first flange; and
a second cell mirror provided to a surface of the second flange so that a mirror surface of the second cell mirror faces to a mirror surface of the first cell mirror, defining an inter-mirror distance between the first and second mirrors.

3. The gas flow cell of claim 2, wherein the first cell mirror is fixed to or formed into a single unit with the first flange.

4. The gas flow cell of claim 3, wherein the first cell mirror comprises a first light-transmission hole let light pass through the first light transmission hole.

5. The gas flow cell of claim 4, wherein a second light-transmission hole is bored in the first flange, and a light transmission window is embedded in a recess cut at rear side of the first cell mirror so that light can pass through the second light transmission hole and the light transmission window, and enters through the light transmission hole to the inside of the cell body.

6. The gas flow cell of claim 2, wherein the second cell mirror is movable against to the second flange so that the inter-mirror distance can be changed.

7. The gas flow cell of claim 6, further comprising:
a support base configured to mount whole of the second cell mirror; and
a liner driver configured to drive the support base along the long axis direction of the cell body.

8. The gas flow cell of claim 2, wherein the second cell mirror is mounted on a support base, which is driven by a liner driver along the long axis direction of the cell body.

9. The gas flow cell of claim 2, wherein the sample-gas introduction port is provided at a location within an allowable distance from the center of the cell body with respect to the long axis direction of the cell body, wherein the allowable distance is about 20% of the inter-mirror distance.

10. The gas flow cell of claim 2, wherein the sample-gas introduction port is connected to a process chamber configured to be vacuum-evacuated to a predetermined processing pressure.

11. The gas flow cell of claim 10, wherein the sample-gas introduction port is provided at a location within a diffusion length of particles generated in the process chamber.

12. A gas flow cell for an optical gas-analysis system, comprising:
a cylindrical cell body;
a sample-gas introduction port configured to introduce sample-gas and a sample-gas exhaust port configured to exhaust the sample-gas, the sample-gas introduction port and the sample-gas exhaust port provided respectively at locations at a substantial center of the cell body with respect to a long axis direction of the cell body, and each of the sample-gas introduction port and the sample-gas exhaust port is aligned along the direction orthogonal to the long axis direction so that the cylindrical cell body, the sample-gas introduction port, and the sample-gas exhaust port together form a cross-shaped configuration;
first and second flanges disposed at both ends of cell body, respectively;
a first cell mirror provided to a surface of the first flange; and
a second cell mirror provided to a surface of the second flange so that a mirror surface of the second cell mirror faces to a mirror surface of the first cell mirror, defining an inter-mirror distance between the first and second mirrors.

13. The gas flow cell of claim 12, wherein each of the sample-gas introduction port and the sample-gas exhaust port is provided at a location within an allowable distance from the center of the cell body with respect to the long axis direction of the cell body, wherein the allowable distance is about 20% of the inter-mirror distance.

14. The gas flow cell of claim 13, wherein displacement length between the central lines of the sample-gas introduction port and the sample-gas exhaust port is within about 20% of the inter-mirror distance.

15. The gas flow cell of claim 13, wherein displacement angle between the central lines of the sample-gas introduction port and the sample-gas exhaust port is within about ±10°.

16. The gas flow cell of claim 12, wherein the sample-gas introduction port is connected to a process chamber configured to be vacuum-evacuated to a predetermined processing pressure.

17. The gas flow cell of claim 16, wherein each of the sample-gas introduction port and the sample-gas exhaust port is provided at a location within a diffusion length of particles generated in the process chamber.

18. An optical gas-analysis system, comprising:
a cylindrical cell body;
a single sample-gas introduction port configured to introduce sample-gas, the single sample-gas introduction port provided at a location at a substantial center of the cell body with respect to a long axis direction of the cell body, and the single sample-gas introduction port being aligned along a direction orthogonal to the long axis direction so that the cylindrical cell body and the single sample-gas introduction port together form a shape of a character T; and
a photo-electric conversion chamber configured to convert optical information from the gas flow cell into electric signals.

19. The optical gas-analysis system of claim 18, further comprising:
first and second flanges disposed at both ends of the cell body, respectively;
a first cell mirror provided to a surface of the first flange; and
a second cell mirror provided to a surface of the second flange so that a mirror surface of the second cell mirror faces to a mirror surface of the first cell mirror, defining an inter-mirror distance between the first and second mirrors.

20. An optical gas-analysis system, comprising:
a cylindrical cell body;
a sample-gas introduction port configured to introduce sample-gas and a sample-gas exhaust port configured to exhaust the sample-gas, the sample-gas introduction port and the sample-gas exhaust port provided respectively at locations at a substantial center of the cell body with respect to a long axis direction of the cell body, and each of the sample-gas introduction port and the sample-gas exhaust port being aligned along the direction orthogonal to the long axis direction so that the cylindrical cell body, the sample-gas introduction port, and the sample-gas exhaust port together form a cross-shaped configuration;
first and second flanges disposed at both ends of cell body, respectively;
a first cell mirror provided to a surface of the first flange;

a second cell mirror provided to a surface of the second flange so that a mirror surface of the second cell mirror faces to a mirror surface of the first cell mirror, defining an inter-mirror distance between the first and second mirrors; and a photo-electric conversion chamber configured to convert optical information from the gas flow cell into electric signals.

* * * * *